United States Patent
Herrmann

(10) Patent No.: US 11,911,149 B2
(45) Date of Patent: *Feb. 27, 2024

(54) TECHNIQUE FOR PROCESSING PATIENT-SPECIFIC IMAGE DATA FOR COMPUTER-ASSISTED SURGICAL NAVIGATION

(71) Applicant: Stryker European Holdings I, LLC, Kalamazoo, MI (US)

(72) Inventor: Florian Herrmann, Schwanau (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/668,912

(22) Filed: Feb. 10, 2022

(65) Prior Publication Data

US 2022/0160261 A1 May 26, 2022

Related U.S. Application Data

(63) Continuation of application No. 16/822,611, filed on Mar. 18, 2020, now Pat. No. 11,298,051.

(30) Foreign Application Priority Data

Mar. 20, 2019 (EP) .................................. 19164051

(51) Int. Cl.
*A61B 5/1171* (2016.01)
*A61B 34/20* (2016.01)
(Continued)

(52) U.S. Cl.
CPC ............ *A61B 5/1171* (2016.02); *A61B 34/20* (2016.02); *G06T 7/60* (2013.01); *G06T 15/08* (2013.01);
(Continued)

(58) Field of Classification Search
CPC ....... A61B 5/1171; A61B 34/20; A61B 34/10; A61B 2034/2055; A61B 2034/101;
(Continued)

(56) References Cited

U.S. PATENT DOCUMENTS

| 6,173,068 B1 | 1/2001 | Prokoski |
| 6,684,093 B2 | 1/2004 | Kuth |

(Continued)

FOREIGN PATENT DOCUMENTS

| DE | 10340064 A1 | 4/2005 |
| DE | 102004049448 A1 | 5/2005 |

(Continued)

OTHER PUBLICATIONS

English language abstract and machine-assisted English translation for DE 10 340 064 extracted from espacenet.com database on May 7, 2020, 23 pages.

(Continued)

*Primary Examiner* — John B Strege
(74) *Attorney, Agent, or Firm* — Howard & Howard Attorneys PLLC

(57) ABSTRACT

A technique for processing patient-specific image data for computer assisted surgical navigation. A database is provided including multiple first data sets of two- or three-dimensional image data. Each first data set is representative of first shape data or first biometric data of a skin surface of at least one patient. The method further comprises obtaining, by an optical camera system, a second data set of two- or three-dimensional image data of a skin surface of a particular patient and deriving second shape data or second biometric data of the skin surface from the second data set. By comparing the second shape data or second biometric data with the first shape data or the first biometric data of one or more first data sets, a similarity score is calculated. A signal (Continued)

generated based on the similarity score triggers one of selection and de-selection of a first data set.

17 Claims, 7 Drawing Sheets

(51) Int. Cl.
*G16H 30/20* (2018.01)
*G06T 7/60* (2017.01)
*G06T 15/08* (2011.01)

(52) U.S. Cl.
CPC ...... *G16H 30/20* (2018.01); *A61B 2034/2055* (2016.02); *G06T 2207/30196* (2013.01)

(58) Field of Classification Search
CPC ........ A61B 2090/364; A61B 2090/371; A61B 90/361; G06T 7/60; G06T 15/08; G06T 2207/30196; G16H 30/20; G16H 30/40; G16H 30/00; G16H 50/30; G16H 50/20; G06K 9/00228; G06K 9/00268; G06K 9/6215
See application file for complete search history.

(56) References Cited

U.S. PATENT DOCUMENTS

| | | | |
|---|---|---|---|
| 7,593,549 B2 | 9/2009 | Reiner | |
| 8,438,182 B2 | 5/2013 | Gillam et al. | |
| 8,784,314 B2 | 7/2014 | Mathew | |
| 8,908,929 B2 | 12/2014 | Bolle et al. | |
| 10,342,500 B2 | 7/2019 | Fujii et al. | |
| 11,200,663 B1 | 12/2021 | Bolton et al. | |
| 11,298,051 B2 * | 4/2022 | Herrmann | G06T 7/60 |
| 2007/0238952 A1 | 10/2007 | Boese et al. | |
| 2011/0130635 A1 | 6/2011 | Ross | |
| 2012/0173576 A1 | 7/2012 | Gillam et al. | |
| 2013/0288215 A1 | 10/2013 | Butler et al. | |
| 2015/0242812 A1 | 8/2015 | Nelson et al. | |
| 2017/0032332 A1 | 2/2017 | Bell | |
| 2017/0215969 A1 | 8/2017 | Zhai et al. | |
| 2020/0297251 A1 | 9/2020 | Herrmann | |

FOREIGN PATENT DOCUMENTS

| | | |
|---|---|---|
| EP | 3138526 A1 | 3/2017 |
| WO | 2007127338 A2 | 11/2007 |
| WO | 2013187461 A1 | 12/2013 |
| WO | 2015024600 A1 | 2/2015 |
| WO | 2016080311 A1 | 5/2016 |

OTHER PUBLICATIONS

English language abstract and machine-assisted English translation for WO 2013/187461 extracted from espacenet.com database on May 7, 2020, 25 pages.

English language abstract for DE 10 2004 049 448 extracted from espacenet.com database on May 7, 2020, 1 page.

English language abstract for WO 2016/080311 extracted from espacenet.com database on May 7, 2020, 2 pages.

Fabry, Thomas et al., "Surface Representations for 3D Face Recognition", Face Recognition, Apr. 1, 2010, pp. 273-294.

Parks, Connie et al., "Biometric Correspondence Between Reface Computerized Facial Approximations and CT-Derived Ground Truth Skin Surface Models Objectively Examined Using an Automated Facial Recognition System", Forensic Science International, vol. 286, Feb. 27, 2018, pp. 8-11.

Parks, Connie et al., "Recognizability of Computer-Generated Facial Approximations in an Automated Facial Recognition Context for Potential Use in Unidentified Persons Data Repositories: Optimally and Operationally Modeled Conditions", Forensic Science International, vol. 291, Oct. 1, 2018, pp. 272-278.

* cited by examiner

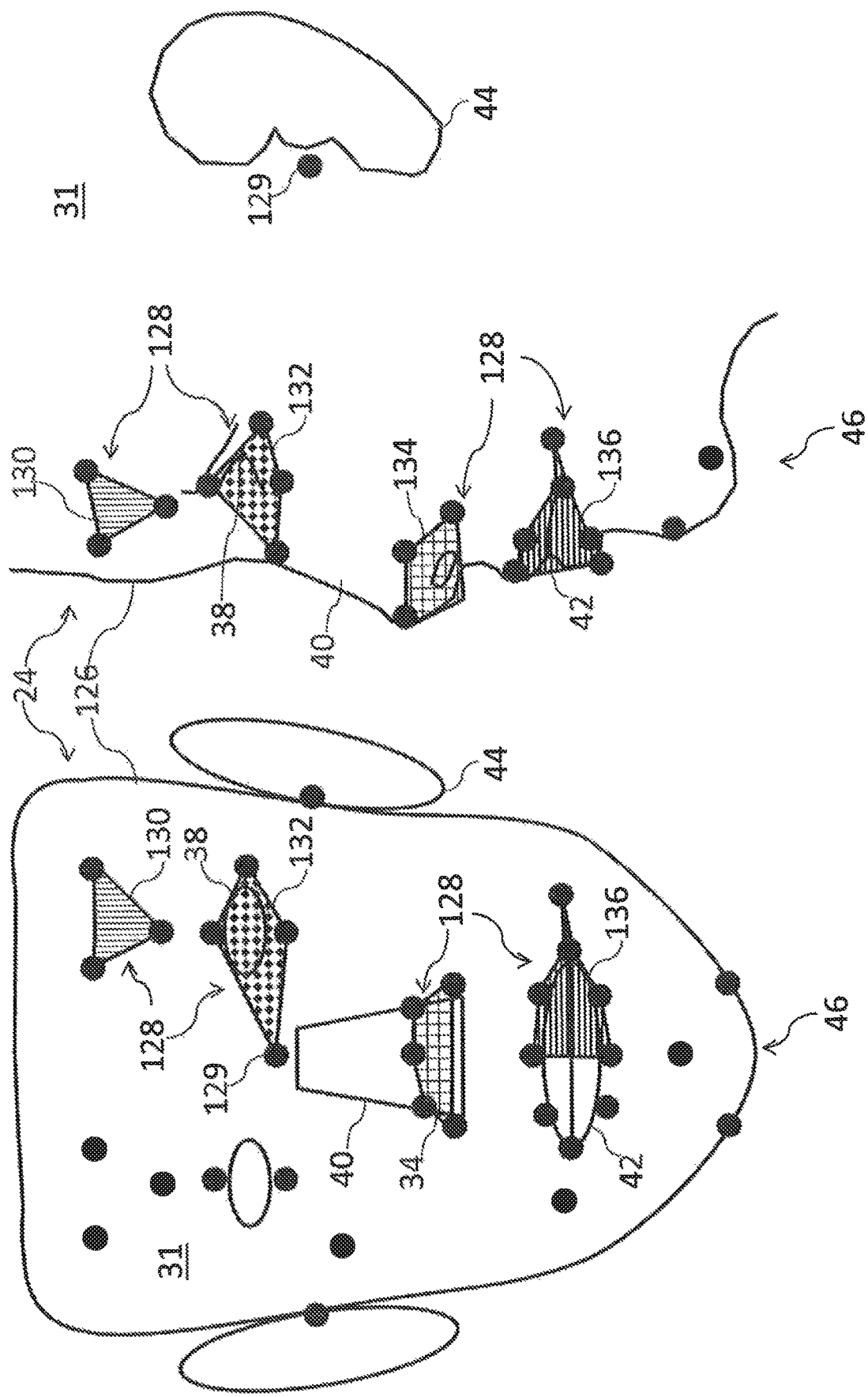

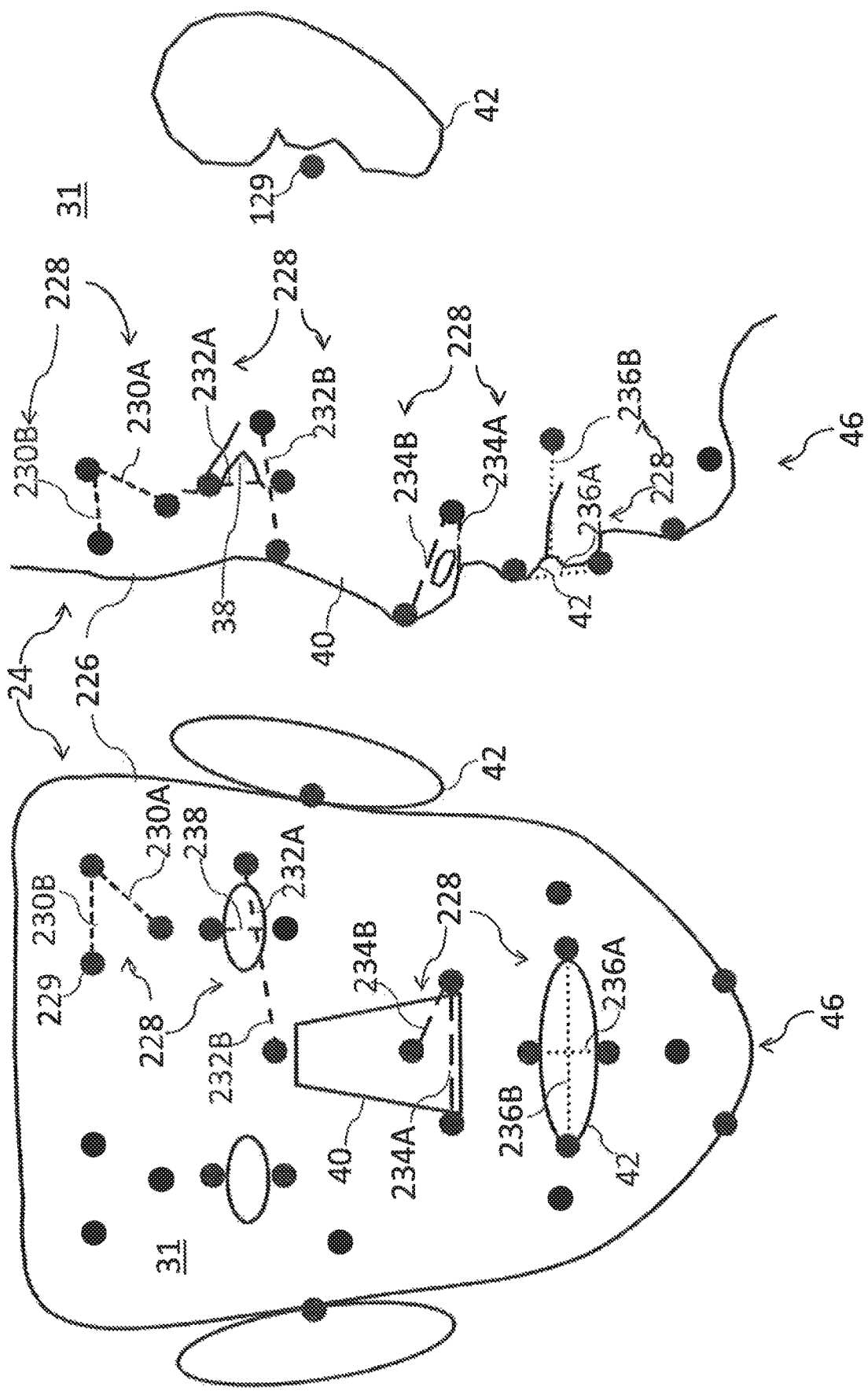

TECHNIQUE FOR PROCESSING PATIENT-SPECIFIC IMAGE DATA FOR COMPUTER-ASSISTED SURGICAL NAVIGATION

PRIORITY CLAIM

This application is a continuation of copending U.S. application Ser. No. 16/822,611, filed Mar. 18, 2020, which claims priority under 35 U.S.C. § 119 to European Patent Application No. 19164051.5, filed Mar. 20, 2019, each of which is hereby incorporated by reference in its entirety.

TECHNICAL FIELD

The present disclosure relates to computer assisted surgical navigation. In particular, a technique for processing patient-specific image data for computer assisted surgical navigation is presented. The technique can be implemented as a method, a computer program product and a surgical navigation system.

BACKGROUND

In computer assisted surgical navigation, three-dimensional image data, obtained for example by a series of computer tomography (CT) scans, are used for assisting the surgical navigation process. These image data are stored in a database and need to be manually selected prior to surgery and assigned to the patient to be treated. This assignment step is usually done using a patient-specific identifier, such as the patient's name.

However, said manual selection and assignment process can be time-consuming and prone to errors. Moreover, the patient may not immediately be identifiable. This situation may occur when an unconscious patient needs to be treated after an accident and no ID documents are available.

A solution to overcome the above stated problems is disclosed in US 2012/0173576 A1. Two-dimensional biometric data of the patient are compared to two-dimensional biometric data stored in a database. These stored biometric data may for example be magnetic resonance imaging (MRI) scans. A face recognition algorithm is applied to the stored biometric data as well as to the biometric data of the patient to derive identification parameters. Then the two sets of identification parameters are compared.

However, two-dimensional biometric data are not always the best basis to compare data sets with one another. In some cases, it is advantageously to use three-dimensional shape data as a basis for the comparison.

SUMMARY

There is a need for a technique to process patient-specific image data in multiple ways to securely identify a data set associated with the patient.

According to one aspect, a method for processing patient-specific image data for computer assisted surgical navigation is presented. The method comprises providing a database comprising multiple first data sets of image data obtained by a medical imaging method, wherein each first data set is representative of first geometric data of a skin surface of at least one patient. The method further comprises obtaining, by an optical camera system, a second data set of image data of a skin surface of a particular patient and deriving second geometric data of the skin surface of the particular patient from the second data set. The method further comprises comparing the second geometric data with the first geometric data of one or more first data sets to calculate a similarity score for each comparison and, based on the similarity score, generating a signal that triggers one of selection and de-selection of a first data set for computer assisted surgical navigation.

The first data set may be obtained as a series of two-dimensional (2D) images (or slices) taken by the medical imaging method. Said images may be processed to create a three-dimensional (3D) representation of a skin surface of the patient from which the images have been taken. The first geometric data may then be derived from or constituted by the three-dimensional representation. A representation of a patient's skin surface may be subdivided into a plurality of 2D and/or 3D geometric structures (e.g., triangles, pyramids, ellipsoids, cylinders or polyeders) constituting the first geometric data. Alternatively, the whole representation of the skin surface may form a single, arbitrarily complex shape. The set of first geometric data may be associated with a patient-specific identifier and stored in the database.

In a first variant, the image data are three-dimensional image data and the first and second geometric data are first and second three-dimensional shape data, respectively. Accordingly, the first and second shape data may be compared by a shape matching algorithm. The shape matching algorithm may search the first shape data for a specific geometric shape contained in the second shape data or vice versa.

In a second variant, the first and second geometric data are first and second biometric data, respectively. Accordingly, the first and second biometric data may be compared by a biometric matching algorithm. The biometric matching algorithm may search the first biometric data for a specific biometric structure contained in the second biometric data or vice versa. The image data may in this case be two- or three-dimensional image data.

The optical camera system may be configured to obtain a two- or three-dimensional image of a skin surface of a patient to be treated. Examples of the optical camera system include a stereo camera. The optical camera system may comprise infrared sensors. Similar to the first geometric data, the second geometric data may be derived from or constituted by the two- or three-dimensional image obtained by the optical camera system.

For calculating the similarity score according to the first variant, one or more of a plurality of geometric shapes in the first shape data may be compared with one or more of a plurality of geometric shapes in the second shape data. Alternatively, when the whole skin surface is represented by a single shape constituting the respective first and second shape data, the similarity score may be calculated based on comparing the shape of two representations of skin surfaces as a whole.

Accordingly, one or more of a plurality of biometric structures in the first biometric data may be compared with one or more of a plurality of biometric structures in the second biometric data for calculating the similarity score in the second variant.

The optical camera system may be configured for tracking a patient or surgical object during computer assisted surgical navigation. Thus, the same optical camera system used for obtaining the 2D or 3D image data of the patient's skin surface may also be used during computer assisted surgical navigation.

The second geometric data (i.e., either shape data or biometric data) may be compared with the first geometric data of a particular first data set that has initially been pre-selected for computer assisted surgical navigation. The pre-selection may have been performed manually. Moreover, generating the signal may comprise evaluating if the similarity score calculated for the pre-selected first data set satisfies a pre-defined condition (e.g., a similarity condition). Depending on a result of the evaluation, the signal may then trigger either selection or de-selection of the pre-selected first data set.

The signal may be a warning signal to a user to trigger de-selection of the pre-selected first data set. Alternatively, the signal may be a confirmation signal to a user to trigger selection of the pre-selected first data set.

The signal may be at least one of an acoustic signal and an optic signal. An acoustic signal may be realized by a beeping sound. An optic signal may be realized by a blinking lamp, a color change effect of a lamp or on a display screen (e.g., of a surgical navigation system).

The second geometric data (i.e., either shape data or biometric data) may be compared with the first geometric data of the multiple first data sets to calculate multiple similarity scores. Moreover, the signal may trigger selection of that one of the multiple first data sets which, based on the multiple similarity scores, is representative of the first geometric data that have the highest similarity with the second geometric data.

The medical imaging method may comprise one of computer tomography (CT) and magnetic resonance imaging (MRI).

The multiple first data sets in the database may have been acquired pre-operatively. Alternatively, or in addition, the second data set may be obtained in an operating room. The multiple first data sets may be obtained by the medical imaging method at a former treatment or a medical examination of the at least one patient and stored in a database. Alternatively, the multiple first data sets may be obtained by the medical imaging method in preparation of the operation, e.g., a day or longer before the actual operation.

The second data set may be obtained by the optical camera system also used for computer assisted surgical navigation. Alternatively, the second data set may be obtained by a first optical camera system, different from a second optical camera system used during operation.

Navigation instructions may be provided on the basis of the selected first data set. For example, when a series of CT scans of a patient's cranium (or other bone) is used to create the selected first data set, said series of CT scans may also be used to guide a surgical instrument relative to the CT scans during the operation.

According to a second aspect, a computer program product is provided. The computer program product comprises program code portions for performing the steps of the method when the computer program product is executed on one or more processors.

According to a further aspect, a surgical navigation system configured to process patient-specific image data is provided. The system comprises an interface configured to access a database comprising multiple sets of first image data obtained by a medical imaging method, wherein each image data set is representative of first geometric data of a skin surface of at least one patient. The system further comprises an optical camera system configured to obtain a second data set of image data of a skin surface of a particular patient. The system further comprises a processing unit configured to derive second geometric data of the skin surface of the particular patient from the second data set, to compare the second geometric data with the first geometric data of one or more first data sets to calculate a similarity score for each first geometric data, and, based on the similarity score, to generate a signal that triggers one of selection and de-selection of a first data set for computer assisted surgical navigation.

The system may further be configured to perform the steps of the method according to the first variant or the second variant described herein.

The optical camera system may comprise at least one of a stereo camera and an infrared 3D sensor.

The system may further comprise a display unit configured to output the signal and/or to provide navigation instructions on the basis of the selected first data set.

BRIEF DESCRIPTION OF THE DRAWINGS

Further details, advantages and aspects of the present disclosure will become apparent from the following embodiments taken in conjunction with the drawings, wherein:

FIGS. 2A/2B illustrate a set of three-dimensional image data representative of first shape data of a skin surface of a patient obtained by a medical imaging method;

FIGS. 3A/3B illustrate a set of two-dimensional image data representative of first biometric data of a skin surface of a patient obtained by a medical imaging method.

DETAILED DESCRIPTION

Figure 1A:
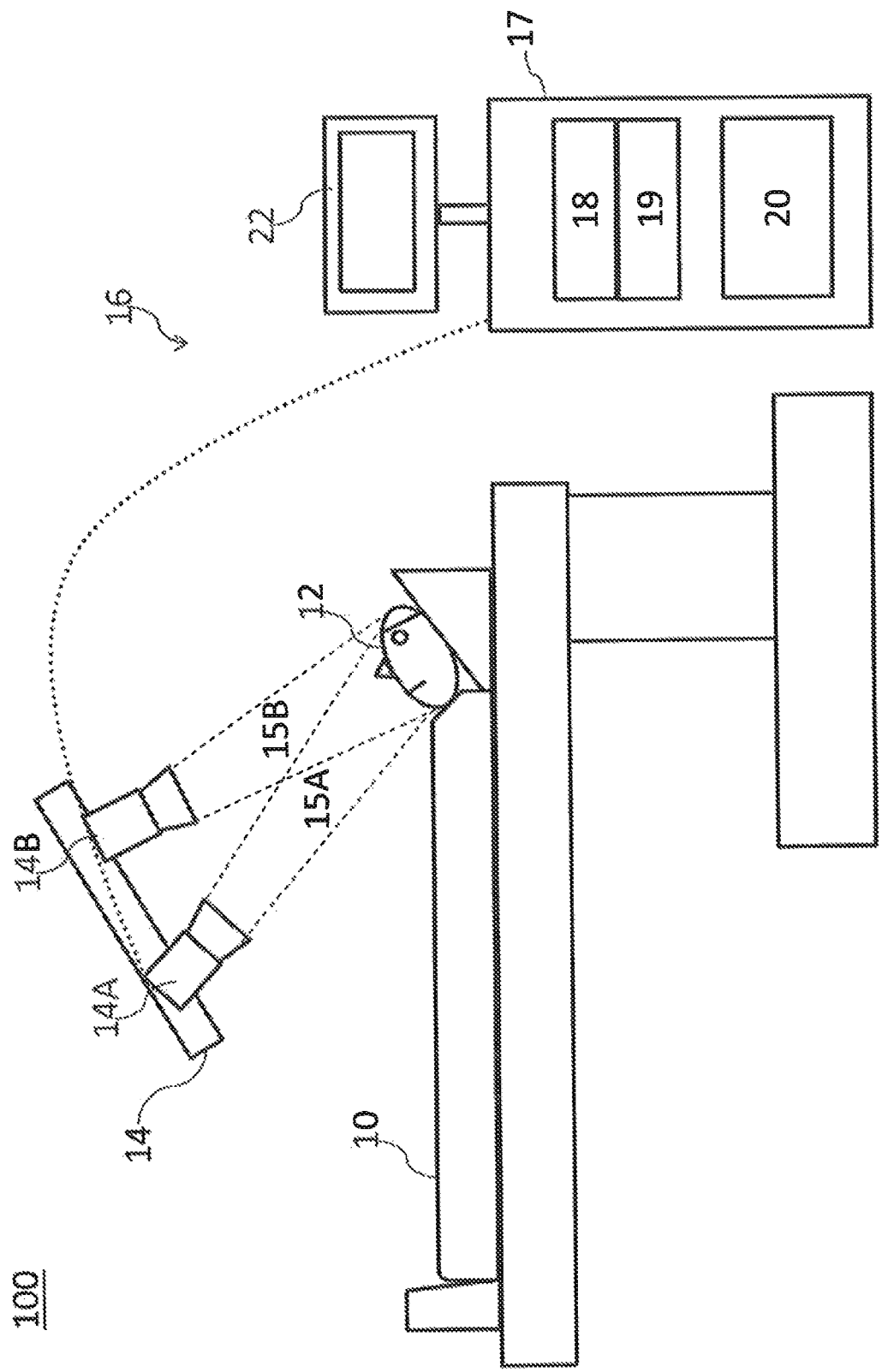
FIG. 1A shows a schematic view of a patient in an operation room and an embodiment of a surgical navigation system comprising an optical camera system configured to obtain a two- or three-dimensional image of the patient's face.

In the following description, exemplary embodiments of a technique for processing patient-specific image data for computer assisted surgical navigation will be explained with reference to the drawings. The same reference numerals will be used to denote the same structural features.

FIG. 1A shows a patient 10 in an operating room 100 prior to or during computer assisted surgery. The patient 10 is imaged by an optical camera system 14, having a field of view 15 that is depicted in FIG. 1A by dashed lines. The optical camera system 14 comprises a stereo camera with two camera units 14A, 14B and is configured to obtain a two- or three-dimensional image of a skin surface of the patient's face 12. Furthermore, in some variants the optical camera system 14 is configured to track the patient or another surgical object, such as a surgical tool, during computer assisted surgical navigation. To this end, an optical tracker (not shown) may have been attached to the patient 10 or the surgical tool. The optical camera system 14 forms part of a surgical navigation system 16 and is connected to a processing unit 17 thereof. The connection is depicted by the dotted curved line in FIG. 1A. The processing system 17 further comprises an interface 18 to access a database 19, a processing unit 20 and a display unit 22.

The database 19 stores multiple first data sets of 2D or 3D image data. Each of the data sets is uniquely associated with one patient. Each data set has been obtained from a particular patient by a medical imaging method, such as CT or MRI. In one embodiment, only two-dimensional images are provided by the medical imaging method. In this case, some or all of these images are processed, either by the processing unit 20 or by another processing device, to create the first data sets with three-dimensional shape data of the skin surface of the particular patient. In another embodiment, the medical imaging method already provides three-dimensional images, in which case no further processing of these images may be necessary to obtain the first data sets of three-dimensional image data. The first data sets have been acquired pre-operatively, either at a former treatment of the patient, a medical examination or during a preparatory step of the surgery. When the method is performed according to the second variant (i.e., processing biometric data), no further processing of the two-dimensional images provided by the medical imaging method may be necessary.

The database 19 and the first data sets stored therein can be accessed by the processing unit 20 or another processing device via the interface 18. The interface 18 is connected to the database 19 by a wired connection, such as a cable, or in a wireless manner, such as a Wi-Fi connection. The database 19 may be external to the processing unit 17.

The display unit 22 is configured to output an optic signal (e.g., on a display screen) and may be further configured to provide navigation instructions to the surgeon during the computer assisted surgery.

Figure 1B:
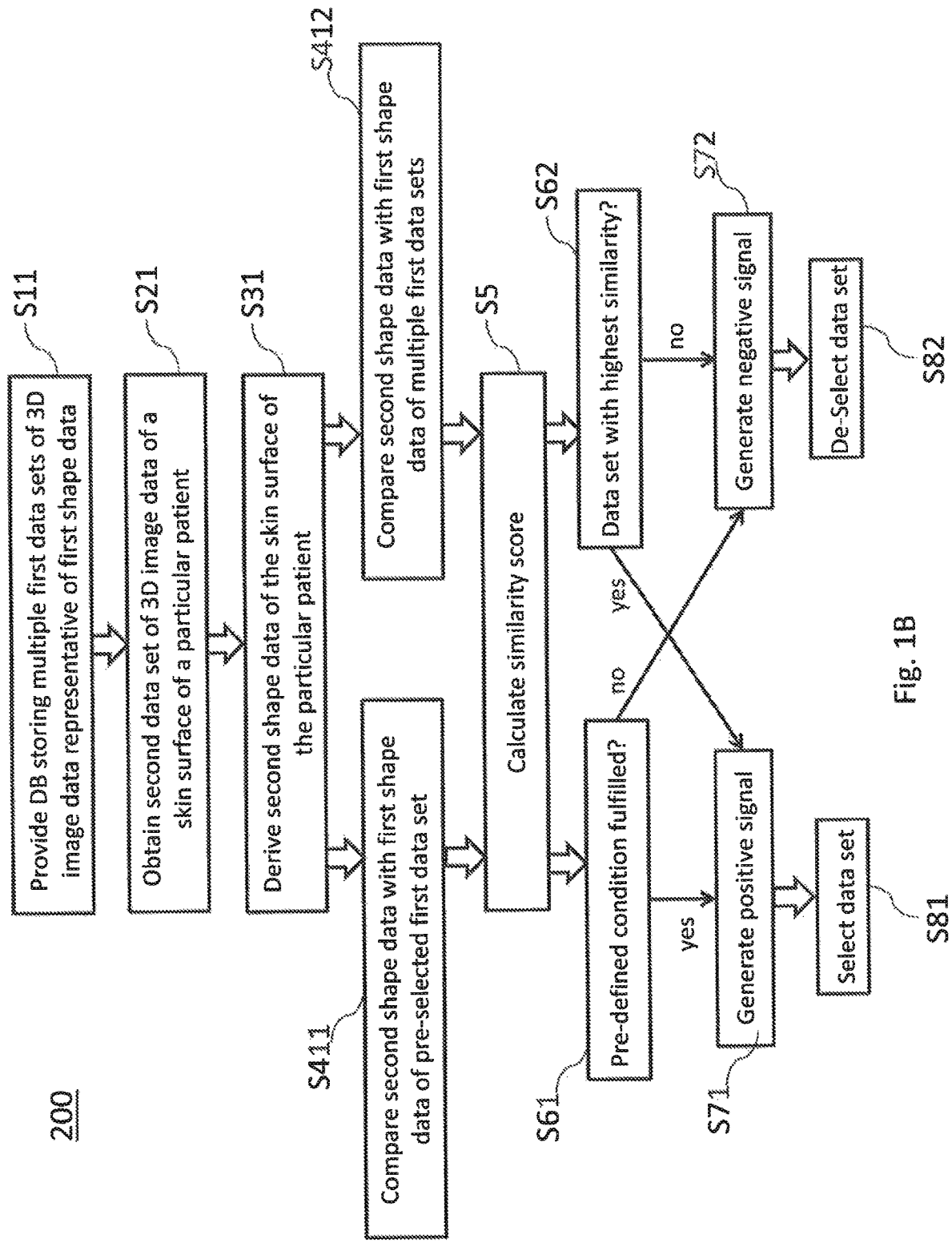
FIG. 1B shows a flow diagram of a first variant of a method for processing patient-specific image data for computer assisted surgical navigation.

FIG. 1B shows a flow diagram 200 of an exemplary embodiment of a method for processing patient-specific image data for computer assisted surgical navigation according to a first variant. The method is performed by the surgical navigation system 16 of FIG. 1A.

The method starts with step S11, wherein the database 19 storing multiple first data sets of three-dimensional image data is provided. Each of the first data sets is representative of first shape data of a skin surface of a specific patient. In step S21, a second data set of three-dimensional image data of a skin surface of the particular patient 10 in the operating room 100 is obtained by the optical camera system 14. From this image data of the second data set, second shape data of the skin surface of the patient 10 are derived by the processing unit 20 in step S31.

The exemplary method depicted in FIG. 1B can be performed either automatically or semi-automatically. Both variants comprise steps S11 to S31.

When performed semi-automatically, a specific first data set has been pre-selected by a user. For example, the patient 10 is identified (e.g., by the patient's name) by the user (e.g., a health care worker preparing the operation) and a specific first data set is selected based on the patient-specific identifier. The first shape data of the pre-selected first data set is then compared in step S411 with the second shape data of the skin surface of the patient 10. A similarity score is then calculated for this comparison in step S5. If the calculated similarity score fulfils a pre-defined condition in step S61, e.g. a minimum similarity, a signal indicative of a positive indication (in the following referred to as "positive signal") is generated in step S71. If it is determined in step S61 that the pre-defined condition is not fulfilled, a signal indicative of a negative indication (in the following referred to as "negative signal") is generated in step S72. A specific data set is selected in step S81 if a positive signal was generated in step S71 for this data set. In the case of the generation of a negative signal (step S72), the specific data set for which the negative signal was generated is de-selected in step S82.

For example, the positive signal may be realized by a green light, a positive message (e.g., "OK") on the display unit 22 or a short beeping sound. Thus, the user is informed that the pre-selected first data set is correctly associated with the patient 10 to be treated and may then load said data set into an application for surgical navigation running on the surgical navigation system 16. In the case of a negative signal, the user may for example be informed by a red light, a negative message (e.g., "NOT ASSOCIATED") on the display unit 22 or a long beeping sound that the pre-selected first data set is not correctly associated with the patient 10. The user may then select another first data set for which the method is replaced or may nevertheless load said data set into the application for surgical navigation.

The automatically performed method variant comprises step S412, wherein the second shape data of the skin surface of the particular patient are compared with first shape data of multiple first data sets of possibly different patients. Similar to the semi-automatically method, a similarity score is calculated for each comparison of first and second shape data in step S5. In step S62, it is checked whether the similarity score associated with a specific first data set defines a maximum value of all calculated similarity scores. If the similarity score of the specific first data set is the highest of all calculated similarity values for a specific second data set, a positive signal is generated in step S71. In all other cases, a negative signal is generated in step S72. Similar to the semi-automatically method variant, a specific first data set is selected (step S81) or de-selected (step S82) depending on the indication of the signal.

For example, it may be indicated to a user which of the multiple first data sets should be selected by displaying the patient-specific identifier assigned to that specific first data set (or an equivalent unique identifier) on the display unit 22. The user may then select said data set and load it into the surgical navigation application. Alternatively, the positively signalled first data set may automatically be loaded into the surgical navigation application. In the case that no first data set was positively signalled, the user may be informed by a red light, a negative message (e.g., "NO DATA SET FOUND") on the display unit 22 or a long beeping sound. The user may then manually select a first data set or may infer that no data set associated with the patient 10 could be found.

Figure 1C:
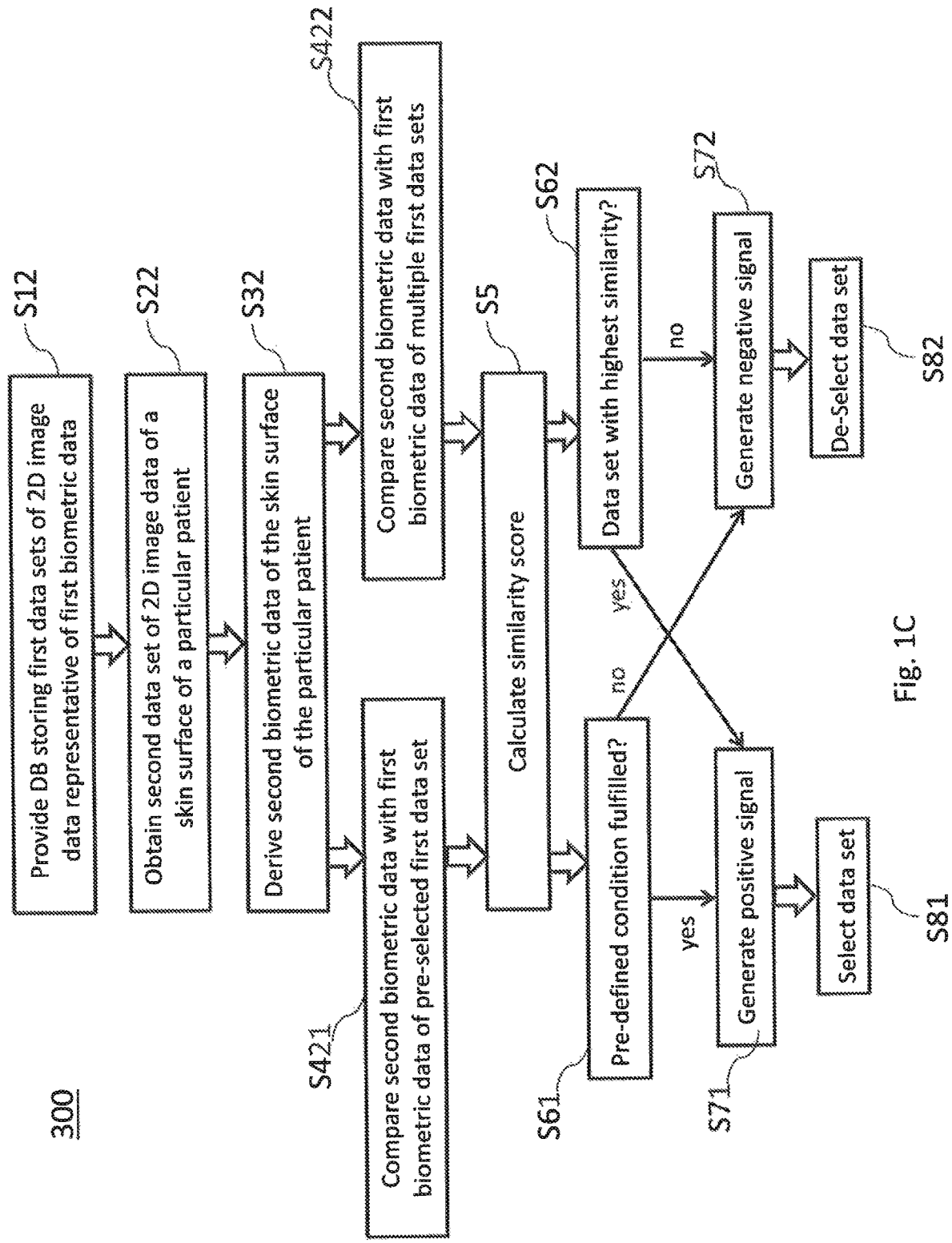
FIG. 1C shows a flow diagram of a second variant of a method for processing patient-specific image data for computer assisted surgical navigation.

FIG. 1C shows a flow diagram 300 of an exemplary embodiment of a method for processing patient-specific image data for computer assisted surgical navigation according to a second variant. The method is performed by the surgical navigation system 16 of FIG. 1A.

The method depicted in FIG. 1C differs from the method depicted in FIG. 1B in the steps S11 to S411 and S412. In step S12 a database 19 storing multiple first data sets of image data is provided. Each of the first data sets is representative of first biometric data of a skin surface of a specific patient. In step S22, a second data set of image data of a skin surface of the particular patient 10 in the operating room 100 is obtained by the optical camera system 14. From this image data of the second data set, second biometric data of the skin surface of the patient 10 are derived by the processing unit 20 in step S32. In step S421, the second biometric data are compared with first biometric data of a pre-selected first data set according to the semi-automatic method described above. If the method according to the second variant is performed automatically, in step S422 the second biometric data is compared with first biometric data of multiple first data sets.

The following steps S5 to S81 and S82 of the method according to the second variant are identical to the steps of the method according to the first variant depicted in FIG. 1B. Thus, further explanation is omitted at this point.

The method steps depicted in FIGS. 1B and 1C will now be explained in greater detail in conjunction with FIGS. 2A to 2C and 3A to 3C, respectively.

FIGS. 2A and 2B show an exemplary embodiment of a representation of a first data set 24 according to the first variant of the presented method. The first data set 24 consists of three-dimensional image data 126 of a particular patient's face, obtained by a CT or MRI scan. FIG. 2A is a front view representation of the image data 126 and FIG. 2B is a side view representation of the image data 126. From this first data set 24, the processing unit 20 of the surgical navigation system 16 or another processing unit derives first shape data 128 of the skin surface of the particular patient.

The embodiment of FIGS. 2A and 2B shows an example wherein the image data 126 of the patient's face are subdivided into a plurality of different three-dimensional shapes. Herein, only the exemplary shapes 130, 132, 134 and 136 of the first shape data 128 are depicted. Shape 130, marked with vertical lines, comprises three surface points 129 at the representation of the left forehead of the patient and has the form of a triangle. Shape 132, marked with black and white diamonds, comprises four surface points 129 around the representation of the left eye 38 of the patient and has the form of a distorted rectangle. Shape 134 is marked with squares and comprises five surface points 129 around the representation of the tip of the nose 40 of the patient. Shape 136 is marked with horizontal lines and comprises six surface points 129 around the left part of the representation of the mouth 42 of the patient. It is to be understood that the shapes 130, 132, 134 and 136 are only schematic and for explanatory purposes and are neither limited to their form, the amount of surface points 129 comprised by them, or to their total amount. For example, additional shapes around the representation of the left ear 44 of the patient or the representation of the chin 46 of the patient can be defined. In an alternative embodiment, the entire image of the patient's face 126 may constitute a single arbitrarily complex shape 31.

In FIG. 2B, the shapes 130, 132, 134 and 136 are depicted in a side view representation of the image data 126. As can be seen, the form of the shapes 130, 132, 134 and 136 differs between front view (FIG. 2A) and side view (FIG. 2B). Thus, it is evident that the shapes 130, 132, 134 and 136 are three-dimensional. Each of the first data sets 24 representing first shape data 128 may be associated with a patient-specific identifier, e.g., the patient's name or a health insurance number, and stored in the database 19 for being accessed or retrieved in step S11. The patient-specific identifier may serve to indicate one or more first data sets 24 associated with the patient 10 to be treated.

Figure 2C:
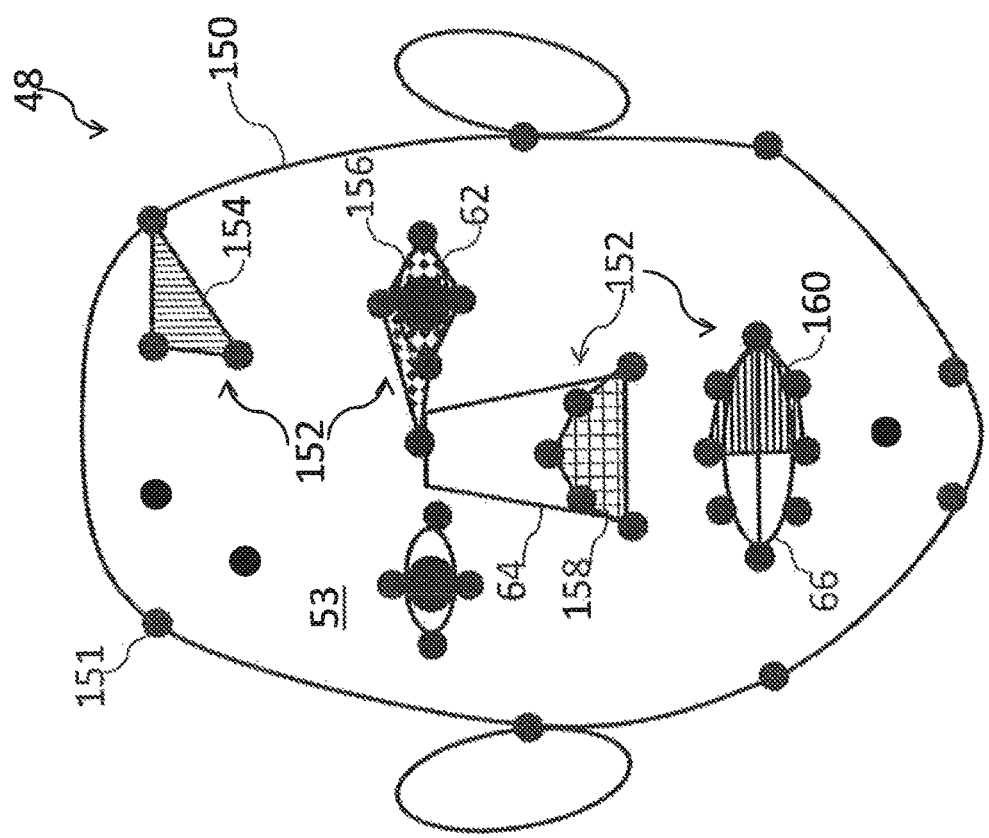
FIG. 2C shows a three-dimensional image of a patient's face obtained by an optical camera system and second shape data of a skin surface of the patient derived from the image.

FIG. 2C shows an exemplary embodiment of a representation of a second data set 48 of three-dimensional image data 150 of a skin surface of the patient 10 to be treated in the operating room 100. The image data 150 have been obtained by the optical camera system 14 according to step S21 in the operating room 100 at the beginning of or during the operation. In the same way as described in conjunction with FIGS. 2A and 2B, second shape data 152 are derived from the second data set 48 by the processing unit 20 of the surgical navigation system 16 according to step S31.

Again, the embodiment of FIG. 2C shows an example wherein the image data 150 of the patient's face is subdivided into a plurality of different shapes. Herein, four exemplary shapes 154, 156, 158 and 160 of the second shape data 152 are depicted in FIG. 2C. The shapes 154, 156, 158 and 160 are located at positions in the image data 150 that correspond to the positions of the shapes 130, 132, 134 and 136 in the image data 126 of FIGS. 2A and 2B. That is, the shape 154 is located at the representation of the forehead of the patient 10, the shape 156 is located around the representation of the left eye 62 of the patient 10, the shape 158 is located around the representation of the tip of the nose 64 of the patient 10 and the shape 160 is located around the representation of the left part of the mouth 66 of the patient 10. Like the shapes 130, 132, 134 and 136 depicted in FIGS. 2A and 2B, the shapes 154, 156, 158 and 160 are only schematic and for exemplary purposes and are neither limited in their form, the amount of surface points 151 comprised by them, or to their total amount. Alternatively, the entire image data 150 may constitute a single arbitrarily complex shape 53.

The shape data 128 stored in the database 19 and the shape data 152 of the patient 10 to be treated are compared by the processing unit 20 using a shape matching algorithm. The shape matching algorithm may be based on one of the following feature detection methods: edge detection, corner detection, blob detection or ridge detection. In more detail, the shape matching algorithm extracts for example the shape 154 from the second shape data 152 and scans the first shape data 128 for a similar shape, located at a similar position. In the embodiment depicted in FIGS. 2A, 2B and 2C, the algorithm would encounter the shape 130 and compare its position and form with the position and form of the original shape 154. According to step S5, a similarity score of the shapes 154 and 130 will then be calculated by the shape matching algorithm and the algorithm will go on to extract the next shape 156 from the second shape data 152 and scan the first shape data 128 for a similar shape. The similarity scores may be calculated based on a variety of parameters, e.g. the location of the shape inside the three-dimensional image, the form of the shape, the amount of surface points comprised by the shape or the overall size of the shape.

Thus, the shape matching algorithm calculates for each shape 154, 156, 158 and 160 of the second shape data 152 a similarity score with at least one shape 130, 132, 134 and 136 of the first shape data 28. The multiple similarity scores may be combined to form a cumulative similarity score for the first shape data 128. The shape matching algorithm calculates in this manner a cumulative similarity score for each of the multiple first shape data sets 24 stored in the database 19.

In an embodiment wherein first and second shape data 128, 152 are not subdivided into shapes as depicted in FIGS. 2A, 2B and 2C, but wherein the entire image data 126, 150 form the respective shape data 31, 53, only one similarity score will be calculated for the pair of shape data 128, 152.

One advantage of subdividing the three-dimensional image data 126, 152 into a plurality of sub-shapes is the fact that the required computational resources of the processing unit 20 can be reduced. As only specific shapes around significant portions of the representation of a human face, such as the eyes, the nose and the mouth are considered by the algorithm, the number of pixels to be compared is reduced. On the other hand, when the shape matching algorithm is applied to the entire representation of the patient's skin surface, the number of pixel-based comparisons and thus the accuracy of the selection method can be increased. In conclusion, the shape matching algorithm has to be adjusted based on the desired degree of accuracy and the desired computation time.

FIGS. 3A and 3B show an exemplary embodiment of a representation of a first data set 24 according to the second variant of the presented method. The first data set 24 consists of image data 226 of a particular patient's face, obtained by a CT or MRI scan. Similar to FIGS. 2A to 2C, FIG. 3A is a front view representation of the image data 226 and FIG. 3B is a side view representation of the image data 226. From this first data set 24, the processing unit 20 of the surgical navigation system 16 or another processing unit derives first biometric data 228 of the skin surface of the particular patient.

Equivalent to FIGS. 2A and 2B, exemplary biometric data 230A, 230B, 232A, 232B, 234A, 234B and 236A, 236B are depicted in FIGS. 3A and 3B. In the depicted example, the biometric data 228 comprise biometric distances, e.g., the diameter 232A of the eye 38 of the patient, the distance between the tip and the base of the patient's nose 234B and the length of the patient's mouth 236B.

Figure 3C:
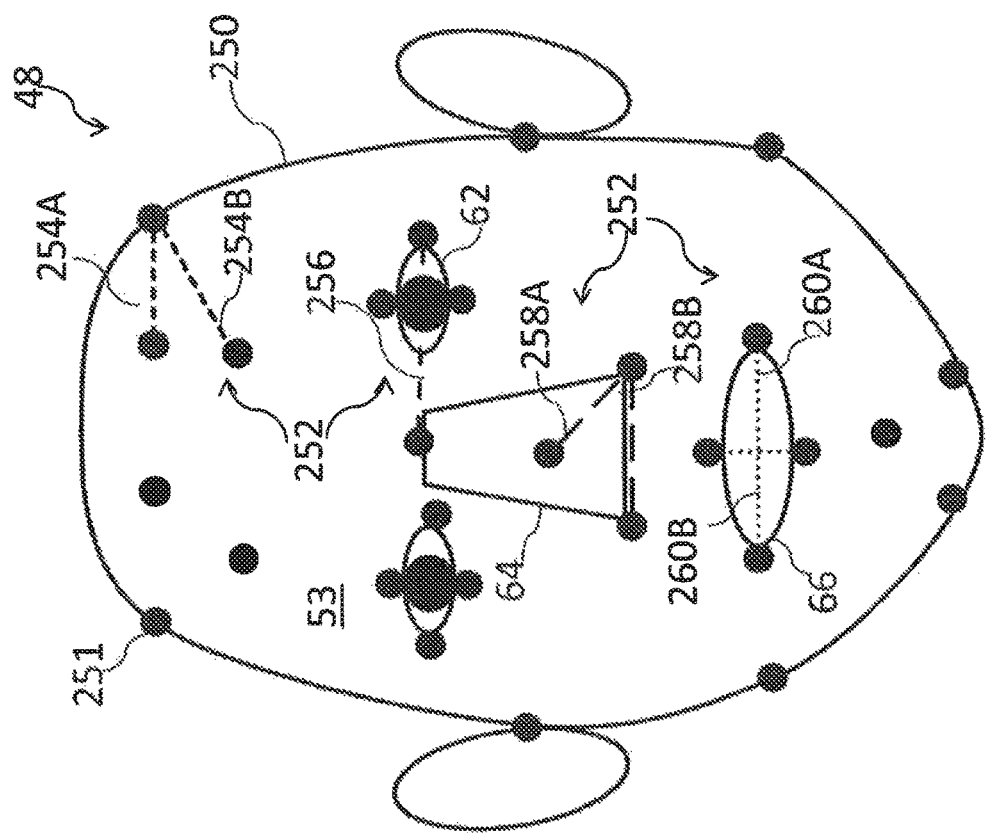
FIG. 3C shows a two-dimensional image of a patient's face obtained by an optical camera system and second biometric data of a skin surface of the patient derived from the image.

Likewise, FIG. 3C shows an exemplary embodiment of a representation of a second data set 48 of image data 250 of a skin surface of the patient 10 to be treated in the operating room 100. The image data 250 have been obtained by the optical camera system 14 according to step S22 in the operating room 100 at the beginning of or during the operation. In the same way as described in conjunction with FIGS. 3A and 3B, second biometric data 252 are derived from the second data set 48 by the processing unit 20 of the surgical navigation system 16 according to step S32. Similar to FIG. 2C, exemplary biometric data, e.g., the biometric distances 254A, 254B, 256, 258A, 258B and 260A, 260B are depicted in FIG. 3C.

The first biometric data 228 are compared with the second biometric data 252 by a biometric algorithm. The algorithm for example measures the distance 254A at a representation of the patient's forehead in the image data 250 and searches for a similar distance at a similar location in the image data 226. In the depicted example, the biometric matching algorithm would encounter the distance 254B at the same location (i.e., at a representation of the patient's forehead) and would compare the distances 254B and 254A. Based on the comparison, the algorithm will then calculate a similarity score for the respective comparison according to step S5 and will then go on equivalently to the shape matching algorithm described with respect to FIGS. 2A to 2C.

As explained with respect to FIGS. 1B and 1C, the method according to both variants can be performed semi-automatically or automatically. This will be described in the following in more detail.

When the method is performed semi-automatically, a particular first data set 24 is initially pre-selected by a user for computer assisted surgical navigation, e.g., via the patient-specific identifier assigned to the data set 24 (step S411, S421). The processing unit 20 in this case calculates a similarity score for the pre-selected data set 24 (step S5) and checks whether the calculated similarity score satisfies a pre-defined condition, such as a minimum similarity (step S61). If the predefined condition is satisfied, a positive (confirmation) signal is generated by the processing unit 20, indicating to the user that the choice of the pre-selected first data set 24 is correct (step S71). If the predefined condition is not satisfied, a negative (warning) signal is generated by the processing unit 20, indicating to the user that the choice of the pre-selected first data set 24 is not correct (step S72). The user is thus triggered to select (step S81) or de-select (step S82) the pre-selected data set 24 as described above.

When the method is performed automatically, the second shape data 152, 252 are compared with the first shape data 128, 228 of multiple first data sets 24 stored on the database 19 (step S412). For each comparison, a similarity score according to step S5 is calculated following the above description. In this case, only the particular first data set 24 having the first shape data 128, 228 that yield the highest similarity score (step S62) will be positively signaled (step S71). All other first data sets 24 will be negatively signaled according to step S72 (or not signaled at all). Based on the positive signal, the processing unit 20 is triggered to select the corresponding first data set 24 out of the plurality of first data sets 24 stored on the database 19 according to step S81. Said first data set 24 is then used to identify the specific patient 10 to be treated and/or to assist the surgery process, e.g., by providing navigation instructions to the surgeon on the display unit 22 relative to a visualization of the selected first data set 24. According to step S82, all other data sets 24 are de-selected by the method.

Especially when the method is performed semi-automatically, the signal may be an optical signal, e.g. a blinking lamp, or an acoustic signal, e.g. a beeping sound. However, also when performing the method automatically, the user may be informed about the result of the comparison by an optical and/or an acoustic signal. For example, when no first data set 24 matching the second data set 48 could be found by the shape matching algorithm, this may be indicated to the user by a negative signal. This may be the case when no medical imaging has been performed for the specific patient 10 to be treated. Thus, the healthcare workers preparing the operation are aware that no CT or MRI scan is available for the specific patient 10, without the need of manually searching through the database 19. In some cases, the patient 10 to be treated may not be identifiable, e.g., when brought to the hospital unconscious after a serious accident. Nevertheless, a first data set 24 matching that patient 10 could still be found by the shape matching algorithm. This case may then be indicated to the user by a positive signal.

Moreover, it is also possible that a first data set 24 is assigned to a wrong patient-specific identifier, e.g., a false patient name. Thus, when manually searching for a first data set 24 matching the second data set 48 for the specific patient 10, the correct dataset may not be identifiable for the user. This disadvantage can be overcome by the technique presented herein as a first data set 24 is selected based on the actual shape data and not on a manually assigned identifier. Additionally, selecting a first data set 24 based on three-dimensional shape data rather than biometric data provides for a higher degree of accuracy of the selection method. Especially for a patient's face, the measurable biometric data are mainly representative of two-dimensional distances, e.g., the inter-pupil distance. However, some of these two-dimensional distances may be equal in two or more first data sets 24. Hence, a biometric algorithm comparing biometric data may not be suitable to identify the correct data set. As a three-dimensional geometric shape is much more unique than a two-dimensional distance, it is very unlikely that the same geometric shape will occur in two different first data sets 24. Thus, the error rate of the data set selection process is minimized.

On the other hand, processing three-dimensional shape data and applying a shape matching algorithm to said data may require many computational resources due to the bigger amount of data that has to be processed. Processing two-dimensional biometric data, such as geometric distances, may be faster and less resource-consuming.

In conclusion, the presented technique offers two different ways of processing patient-specific image data. Depending on the desired degree of accuracy and the available computational resources, a user is free to choose between both ways.

While exemplary realisations of a method and a surgical navigation system for processing patient specific image data have been described, it will be understood that the method and the system can be modified in many ways. Therefore, the present disclosure is only limited by the claims appended hereto.

The invention claimed is:

1. A method for processing patient-specific image data for computer assisted surgical navigation, the method comprising:
   providing a database comprising multiple first data sets of three-dimensional image data obtained by a medical imaging method, wherein each first data set is representative of first geometric data of a skin surface of at least one patient;
   pre-selecting a particular first data set among the multiple first data sets of three-dimensional image data for computer assisted surgical navigation;
   obtaining, by an optical camera system, a second data set of two-dimensional or three-dimensional image data of a skin surface of a particular patient;
   deriving second geometric data of the skin surface of the particular patient from the second data set;
   comparing the second geometric data of the skin surface with the first geometric data of the skin surface of the particular first data set to calculate a similarity score for the comparison; and
   based on the similarity score, generating a signal that triggers one of selection and de-selection of the particular first data set for computer assisted surgical navigation.

2. The method of claim 1, wherein:
   the first and second geometric data are first and second biometric data, respectively; and
   the first and second biometric data are compared by a biometric matching algorithm.

3. The method of claim 1, wherein the optical camera system is configured for tracking a patient or surgical object during computer assisted surgical navigation.

4. The method of claim 1, wherein:
   the step of generating the signal comprises evaluating if the similarity score calculated for the pre-selected first data set satisfies a pre-defined condition, wherein, depending on a result of the evaluation, the signal triggers either selection or de-selection of the pre-selected first data set.

5. The method of claim 4, wherein the signal is one of a warning signal to a user to trigger de-selection of the pre-selected first data set and a confirmation signal to a user to trigger selection of the pre-selected first data set.

6. The method of claim 1, wherein the signal is at least one of an acoustic signal and an optic signal.

7. The method of claim 1, wherein:
   the second geometric data is compared with the first geometric data of the multiple first data sets to calculate multiple similarity scores; and
   the signal triggers selection of that one of the multiple first data sets which, based on the multiple similarity scores, is representative of the first geometric data that have the highest similarity with the second geometric data.

8. The method of claim 1, wherein the medical imaging method comprises one of computer tomography and magnetic resonance imaging.

9. The method of claim 1, wherein the multiple first data sets in the database have been acquired pre-operatively and/or the second data set is obtained in an operating room.

10. The method of claim 1, further comprising providing navigation instructions on the basis of the selected one of the first data sets.

11. A computer program product comprising non-transitory computer-readable medium comprising program code portions for performing the method of claim 1 when the computer program product is executed on one or more processors.

12. A surgical navigation system configured to process patient-specific image data, the system comprising:
    an interface configured to access a database comprising multiple sets of three-dimensional first image data obtained by a medical imaging method, wherein each image data set is representative of first geometric data of a skin surface of at least one patient;
    an optical camera system configured to obtain a second data set of two-dimensional or three-dimensional image data of a skin surface of a particular patient; and
    a processing unit configured to:
      receive a pre-selection of a particular first data set among the multiple first data sets of three-dimensional image data for computer assisted navigation;
      derive second geometric data of the skin surface of the particular patient from the second data set;
      compare the second geometric data of the skin surface with the first geometric data of the skin surface of the particular first data set to calculate a similarity score for each comparison; and
      based on the similarity score, to generate a signal that triggers one of selection and de-selection of the particular first data set for computer assisted surgical navigation.

13. The system of claim 12, wherein the optical camera system comprises at least one of a stereo camera and an infrared 3D sensor.

14. The system of claim 12, further comprising a display unit configured to at least one of output the signal and provide navigation instructions on the basis of the selected one of the first data sets.

15. The system of claim 12, wherein:
    the first and second geometric data are first and second biometric data, respectively; and
    the processing unit is configured to compare the first and second biometric data by a biometric matching algorithm.

16. The system of claim 12, wherein the processing unit is further configured to evaluate if the similarity score calculated for the pre-selected first data set satisfies a pre-defined condition, wherein, depending on a result of the evaluation, the signal is configured to trigger either selection or de-selection of the pre-selected first data set.

17. The system of claim 12, wherein the processing unit is further configured to compare the second geometric data with the first geometric data of the multiple first data sets to calculate multiple similarity scores, and trigger selection of that one of the multiple first data sets which, based on the multiple similarity scores, is representative of the first geometric data that have the highest similarity with the second geometric data.

* * * * *